US006828304B1

(12) United States Patent
Burman et al.

(10) Patent No.: US 6,828,304 B1
(45) Date of Patent: Dec. 7, 2004

(54) PEPTIDES FOR TREATMENT OF CANCER

(75) Inventors: Anand C. Burman, Ghaziabad (IN); Sudhanand Prasad, Ghaziabad (IN); Rama Mukherjee, Ghaziabad (IN); Manu Jaggi, Ghaziabad (IN); Anu T. Singh, Ghaziabad (IN); Rajan Sharma, Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 87 days.

(21) Appl. No.: 09/630,345

(22) Filed: Jul. 31, 2000

(51) Int. Cl.⁷ .................. A61K 38/00; A61K 38/04; C07K 17/00
(52) U.S. Cl. ............... 514/16; 514/14; 514/15; 530/327; 530/328; 530/329
(58) Field of Search .............. 514/16, 14, 15; 530/329, 327, 328

(56) References Cited

U.S. PATENT DOCUMENTS

| | | | |
|---|---|---|---|
| 4,605,641 A | 8/1986 | Bolin et al. | 514/12 |
| 4,734,400 A | 3/1988 | Bolin et al. | 514/12 |
| 4,835,252 A | 5/1989 | Musso et al. | 530/324 |
| 4,866,039 A | 9/1989 | Wootton et al. | 514/12 |
| 5,141,924 A | 8/1992 | Bolin | 514/12 |
| 5,217,953 A | 6/1993 | Fridkin et al. | 514/12 |
| 5,376,637 A | 12/1994 | Sawai et al. | 514/12 |
| 5,428,015 A | 6/1995 | Kurono et al. | 514/12 |
| 5,565,424 A | 10/1996 | Gozes et al. | 514/12 |
| 5,677,419 A | 10/1997 | Bolin et al. | 530/317 |
| 5,849,261 A | 12/1998 | Dean et al. | 424/1.69 |
| 6,007,792 A | 12/1999 | Dean et al. | 424/1.69 |
| 6,492,330 B1 * | 12/2002 | Mukherjee et al. | 514/12 |

FOREIGN PATENT DOCUMENTS

| | | |
|---|---|---|
| EP | 0354992 | 2/1990 |
| EP | 0835662 | 4/1998 |
| WO | 0023096 | 4/2000 |

OTHER PUBLICATIONS

H. Frucht et al.; Characterization of Functional Receptors for Gastrointestinal Hormones on Human Colon Cancer Cells; Cancer Research 52; 1114–1122; Mar. 1, 1992.

Irene Virgolini et al.; Vasoactive Intestinal Peptide–Receptor Imagine for the Localization of Intestinal . . . Tumors; New England Journal of Medicine; vol. 331 (17); 1116–1121; Oct. 27, 1994.

G.Lilling et al.; Inhibition of Human Neuroblastoma Growth by a Specific VIP Antagonist; Journal of Molecular Neuroscience; vol. 5, 1994/1995; 231–239.

Gozes et al.; Vasoactive Intestinal Peptide Potentiates Sexual Behavior; Inhibition by Novel Antagonist Endocrinology; vol. 125, No. 6; 2945–2949; (1989).

* cited by examiner

*Primary Examiner*—Jon P. Weber
*Assistant Examiner*—Abdel A. Mohamed
(74) *Attorney, Agent, or Firm*—Ladas & Parry

(57) ABSTRACT

This invention relates to novel antiproliferative and anti secrectory peptides that are inhibitory to vasoactive intestinal peptide receptor and are useful in the treatment of cancer. The invention particularly relates to the synthesis of lipid-peptide conjugates containing fatty acids of different sizes, which inhibits the binding of VIP to its receptors. The invention encompasses methods for generation of these peptides, composition containing these peptides and the pharmacological applications of these peptides especially in the treatment and prevention of cancer.

19 Claims, 1 Drawing Sheet

PEPTIDES FOR TREATMENT OF CANCER

FIELD OF INVENTION

This invention relates to novel antiproliferative and anti secrectory peptides that are inhibitory to vasoactive intestinal peptide receptor and are useful in the treatment of cancer. The invention particularly relates to the synthesis of lipid-peptide conjugates containing fatty acids of different sizes, which inhibits the binding of VIP to its receptors. The invention encompasses methods for generation of these peptides, composition containing these peptides and the pharmacological applications of these peptides especially in the treatment and prevention of cancer.

BACKGROUND OF THE INVENTION

Vasoactive intestinal peptide (VIP) is a 28-amino acid neuropeptide, which was first isolated from the porcine intestine (Said, S. I. and Mutt, V., Science, 169, 1217–1218, 1970.) VIP acts as growth factor and plays dominant autocrine and paracrine role in the sustained proliferation of cancer cells. (Said, S. I., Peptides, 5, 143–150, 1984.) Gozes et al. have shown that VIP can serve as autocrine growth factor in lung tumors. (Gozes et al. Biomed. Res. 13 (suppl.2) 37, 1992).

The peptide sequence Leu-Met-Tyr-Pro-Thr-Tyr-Leu-Lys (SEQ ID NO: 1) is reported to be receptor binding inhibitor of vasoactive intestinal peptide (Said, & Mutt, Ann. N.Y. Acad. Sci., 1, 527, 1988). The role this octapeptide as VIP receptor binding inhibitor has been described in the U.S. Pat. No. 5,217,953. In our U.S. patent application Ser. No. 08/727,679 we have described the anti cancer role of this VIP binding receptor inhibitor in combination with other neuropeptide analogs. In another U.S. patent application Ser. No. 09/248,382 we have described the novel analogs of this VIP receptor binding inhibitor incorporating dialkylated amino acids. Keeping in view that lipophilization of bioactive peptides improves their stability, bioavailability and the ability to permeate biomembranes (Dasgupta, P. et al.; 1999, Pharmaceutical Res. 16, 1047–1053; Gozes, I. et al., 1996, Proc. Natl. Acad. Sci. USA, 93, 427–432.), in the present invention we have synthesized lipid conjugates of the peptide sequence Leu-Met-Tyr-Pro-Thr-Tyr-Leu-Lys (SEQ ID NO: 1) using fatty acids of different sizes, C2–C16 carbon atoms, at the N-terminal site of the peptide. Throughout the application the following abbreviation are used with the following meanings:

BOP: Benzotriazole-1-yl-oxy-tris-(dimethylamino)-phosphonium hexofluorophospate

PyBOP: Benzotriazole-1-yl-oxy-tris-pyrrolidino-phosphonium hexofluorophospate

HBTU: O-Benzotriazole-N,N,N',N'-tetramethyl-uronium-hexofluoro-phosphate

TBTU: 2-(1H-Benzotriazole-1yl)-1,1,3,3,-tetramethyluronium tetrafluoroborate

| | |
|---|---|
| HOBt: | 1-Hydroxy Benzotriazole |
| DCC: | Dicyclohexyl carbodiimide |
| DIPCD: | Diisopropyl carbodiimide |
| DIEA: | Diisopropyl ethylamine |
| DMAP: | 4-Dimethylamino pyridine |
| DMF: | Dimethyl formamide |
| DCM: | Dichloromethane |
| NMP: | N-Methyl-2-pyrrolidinone |
| TFA: | Trifluoroacetic acid |

Throughout the specification and claims, the amino acids residues are designated by their standard abbreviations. Amino acids denote L-configuration unless otherwise indicated by D or DL appearing before the symbol and separated from it by hyphen.

Throughout the specification and claims, the amino acids residues are designated by their standard abbreviations. Amino acids denote L-configuration unless otherwise indicated by D or DL appearing before the symbol and separated from it by hyphen.

SUMMARY OF THE INVENTION

The present invention relates to peptides of the following general formula

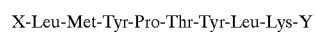

X-Leu-Met-Tyr-Pro-Thr-Tyr-Leu-Lys-Y wherein,

X is acetyl or straight, branched, or cyclic alkanoyl group of from 3–16 carbon atoms.

Y is a carboxy terminal residue selected from OH or amino; or a pharmaceutical acceptable salt of the peptides.

DETAILED DESCRIPTION OF THE INVENTION

Figure 1:
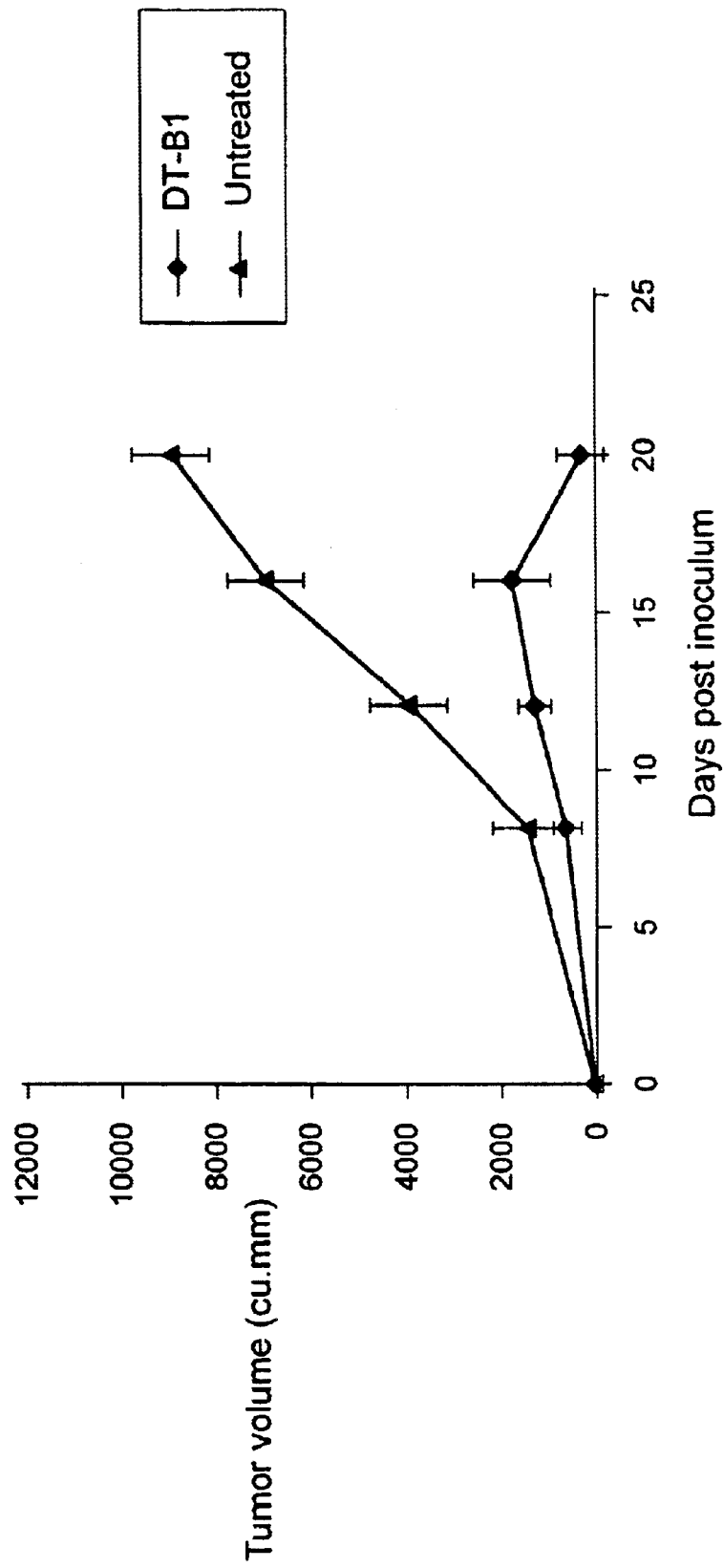
FIG. 1 shows the anti-cancer activity of the peptide DT-B1 on PCT xenograft.

The present invention relates to peptides of the following general formula

X-Leu-Met-Tyr-Pro-Thr-Tyr-Leu-Lys-Y (SEQ ID NO:7)

wherein,

X is acetyl or straight, branched, or cyclic alkanoyl group of from 3–16 carbon atoms.

Y is a carboxy terminal residue selected from OH or amino; or a pharmaceutical acceptable salt of the peptides.

The preferred alkanoyl groups are acetyl, n-butanoyl, n-hexanoyl, n-octanoyl, lauroyl, myristoyl, palmitoyl, isohexanoyl, cyclohexanoyl, _cyclopentylcarbonyl, n-heptanoyl, n-decanoyl, n-undecanoyl, and 3,7-dimethyloctanoyl.

Salts encompassed within the term "pharmaceutically acceptable salts" refer to non-toxic salts of the compounds of this invention. Representative salts and esters include following: acetate, ascorbate, benzenesulfonate, benzoate, bicarbonate, bisulfate, bitartrate, borate, camsylate, carbonate, citrate, dihydrochloride, methanesulfonate, ethanesulfonate, p-toluenesulfonate, cyclohexylsulfamate, quinate, edetate, edisylate, estolate, esylate, fumarate, gluconate, glutamate, glycerophophates, hydrobromide, hydrochloride, hydroxy-naphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate and valerate.

Other salts include Ca, Li, Mg, Na, and K salts; salts of amino acids such as lysine or arginine; guanidine, diethanolamine or choline; ammonium, substituted ammonium salts or aluminum salts.

The salts are prepared by conventional methods.

The preferred lipo-peptide analogs are:

Acetyl-Leu-Met-Tyr-Pro-Thr-Tyr-Leu-Lys-OH (DT-A1) (SEQ ID NO: 2)

n-Butanoyl-Leu-Met-Tyr-Pro-Thr-Tyr-Leu-Lys-OH (DT-B1) (SEQ ID NO: 3)

n-Octanoyl-Leu-Met-Tyr-Pro-Thr-Tyr-Leu-Lys-OH (DT-O1) (SEQ ID NO: 4)

Myristoyl-Leu-Met-Tyr-Pro-Thr-Tyr-Leu-Lys-OH (DT-M1) (SEQ ID NO: 5)

Palmitoyl-Leu-Met-Tyr-Pro-Thr-Tyr-Leu-Lys-OH (DT-P1) (SEQ ID NO: 6)

The novel compounds of the present invention have important pharmacological applications. They are potent anti-neoplastic agents and thereby possess therapeutic potential in a number of human cancers.

The lipopeptides in the present invention have been generated by using solid phase techniques or by a combination of solution phase procedures and solid phase techniques or by fragment condensation. The methods for the chemical synthesis of polypeptides are well known in the art (Stewart and Young, 1969 Solid Phase Synthesis, W. H. Freeman Co.).

In a preferred embodiment of the present invention the peptides were synthesized using the Fmoc strategy, on a semi automatic peptide synthesizer (CS Bio, Model 536), using optimum side chain protection. The peptides were assembled from C-terminus to N-terminus. Peptides amidated at the carboxy-terminus were synthesized using the Rink Amide resin. The loading of the first Fmoc protected amino acid was achieved via an amide bond formation with the solid support, mediated by Diisopropylcarbodiimde (DIPCDI) and HOBt. Substitution levels for automated synthesis were preferably between 0.2 and 0.6 mmole amino acid per gram resin. The steps involved in the synthesis of the peptide analogs employed the following protocol:

TABLE I

| STEP | REAGENT | MIX TIME (MIN) | NO. OF CYCLES |
| --- | --- | --- | --- |
| 1. | Methylene chloride | 1 | 2 |
| 2. | Dimethyl formamide | 1 | 1 |
| 3. | 20% Piperidine in Dimethyl formamide | 1 | 1 |
| 4. | 20% Piperidine in Dimethyl formamide | 29 | 1 |
| 5. | Dimethyl formamide | 1 | 3 |
| 6. | Isopropanol | 1 | 2 |
| 7. | Methylene chloride | 1 | 2 |
| 8. | Amino Acid | Variable | 1 |
| 9. | Dimethyl formamide | 1 | 2 |
| 10. | Stop or Return for next cycle | | |

In a particularly preferred embodiment of the present invention the following chemical moieties were used to protect reactive side chains of the peptides during the synthesis procedure:

The N-terminal amino group was protected by 9-fluorenylmethoxy-carbonyl (Fmoc) group. The hydroxyl-groups of Threonine and Tyrosine were preferably protected by t-butyl group (tBu). Leu, Met and Pro were used unprotected.

In a preferred embodiment of the invention, 2–8 equivalents of Fmoc protected amino acid per resin nitrogen equivalent were used. The activating reagents used for coupling amino acids to the resin, in solid phase peptide synthesis, are well known in the art. These include DCC, DIPCDI, DIEA, BOP, PyBOP, HBTU, TBTU, and HOBt. Preferably, DCC or DIPCDI/HOBt or HBTU/HOBt and DIEA were used as activating reagents in the coupling reactions. The protected amino acids were either activated in situ or added in the form of preactivated esters known in the art such as N-hydroxy succinamide esters, pentafluorophenyl esters etc. The coupling reaction was carried out in DMF, DCM or NMP or a mixture of these solvents and was monitored by Kaiser test [Kaiser et al., Anal. Biochem., 34, 595–598 (1970)]. In case of a positive Kaiser test, the appropriate amino acid was re-coupled using freshly prepared activated reagents.

After the assembly of the peptide analog was completed, the amino-terminal Fmoc group was removed using steps 1–6 of the above protocol and then the peptide-resin was washed with methanol and dried. The analogs were then deprotected and cleaved from the resin support by treatment with trifluoroacetic acid, crystalline phenol, ethanedithiol, thioanisole and de-ionized water for 1.5 to 5 hours at room temperature. The crude peptide was obtained by precipitation with cold dry ether, filtered, dissolved, and lyophilized.

The resulting crude peptide was purified by preperative high performance liquid chromatography (HPLC) using a LICHROCART® $C_{18}$ (250. Times. 10) (reverse phase C-18 column)) reverse phase column (Merck, Darmstadt, Germany) on a Preparative HPLC system (Shimadzu Corporation, Japan) using a gradient of 0.1% TFA in acetonitrile and water. The eluted fractions were reanalyzed on Analytical HPLC system (Shimadzu Corporation, Japan) using a $C_{18}$ LICHROSPHER®, WP-300 (300×4) (reverse phase C-18 column) reverse-phase column. Acetonitrile was evaporated and the fractions were lyophilized to obtain the pure peptide. The identity of each peptide was confirmed by electron-spray mass spectroscopy.

An analog of the present invention can be made by exclusively solid phase techniques, by partial solid phase/solution phase techniques and/or fragment condensation. Preferred, semi-automated, stepwise solid phase methods for synthesis of peptides of the invention are provided in the examples discussed in the subsequent section of this document.

The present invention will be further described in detail with reference to the following examples, as will be appreciated by a person skilled in the art is merely illustrative and should not be construed as limiting. Various other modifications of the invention will be possible without departing from the spirit and scope of the present invention.

Synthesis of Peptides

First Loading on Wang Resin

A typical preparation of the Fmoc-Lys-Wang Resin was carried out using 1.0 g of 4-Hydroxyinethylphenoxy Resin 1% DVB cross-linked resin (0.7 mM/g) (100–200 mesh), procured from Advanced Chemtech, Louisville, Ky., U.S.A. Swelling of the resin was typically carried out in dichloromethane measuring to volumes 10–40 ml/g resin. The resin was allowed to swell in methylene chloride (2×25 ml, for 10 min.). It was washed once in dimethylformamide (DMF) for 1 min. All solvents in the protocol were added in 20 ml portions per cycle. For loading of the first amino acid on hydroxyl group of the resin, the first amino acid, was weighed in three to six fold excess, along with a similar fold excess of HOBt, in the amino acid vessel of the peptide synthesizer. These were dissolved in dimethylformamide (A.C.S. grade) (J. T. Baker, New Jersey, U.S.A.) and activated with DIPCDI and 4-dimethyl amino pyridine (DMAP), just prior to the addition to the resin in the reaction vessel of the peptide synthesizer. The coupling reaction was carried out for a period ranging from 6 hours. The loading of the amino acid on the resin was confirmed by the weight gain of the resin. The loading efficiency was ascertained by the increase of weight of the resin after the addition of the amino acid.

EXAMPLE 1

Synthesis of Acetyl-Leu-Met-Tyr-Pro-Thr-Tyr-Leu-Lys-OH (DT-A1) (SEQ ID NO: 2)

The synthesis of peptide DT-A1 was initiated by using resin loaded with Fmoc-Lys-OH as prepared above on 1 g scale. It was subjected to stepwise deprotection and coupling steps as in steps 1–10 of the synthesis cycle. In each coupling reaction, a four-fold excess of appropriate Fmoc amino acid, DIPCDI and HOBt were used. The average coupling time for each amino acids was between 2–5 hrs. On completion of synthesis and removal of the N-terminal Fmoc protecting group (steps 1–6 of the synthesis cycle), the peptideresin was washed twice with methanol. It was further coupled with acetic anhydride in DMF using DIPCDI and HOBt as coupling agents. This was subjected to cleavage in a cleavage mixture consisting of trifluoroacetic acid and scavengers, crystalline phenol, thioanisole, ethanedithol and water for a period of 1–4 hours at room temperature with continuous stirring. The peptide was precipitated using cold dry ether to obtain the crude peptide. The crude peptide was purified on a $C_{18}$ preparative reverse phase HPLC column (250×10) on a gradient system comprising acetonitrile and water in 0.1% TFA as described previously, in the art. The prominent peaks were collected and lyophilized, reanalyzed on analytical HPLC and subjected to mass spectrometry. There was a good agreement between the observed molecular weight and calculated molecular weight (calculated mass=~1070; observed mass=1071.1). The pure peptide was then used for bioassays.

EXAMPLE 2

Synthesis of n-Butanoyl-Leu-Met-Tyr-Pro-Thr-Tyr-Leu-Lys-OH (DT-B1) SEQ ID NO: 3

The above peptide sequence was synthesized on resin in a similar way as described in Example 1 except n-butyric anhydride is used in place of acetic anhydride. The final purified peptide was further analyzed by mass spectroscopy. The calculated mass and observed mass was in good agreement (calculated mass=~1098, observed mass=1099.3).

EXAMPLE 3

Synthesis of n-Octanoyl-Leu-Met-Tyr-Pro-Thr-Tyr-Leu-Lys-OH (DT-O1 (SEQ ID NO: 4)

The above peptide sequence was synthesized on resin in a similar way as described in Example 1 except octanoic acid is used in place of acetic anhydride. The final purified peptide was further analyzed by mass spectroscopy. The calculated mass is ~1154 and observed mass is 1155.2.

EXAMPLE 4

Synthesis of Myristoyl-Leu-Met-Tyr-Pro-Thr-Tyr-Leu-Lys-OH (DT-M1) (SEQ ID NO: 5)

The above peptide sequence was synthesized on resin in a similar way as described in Example 1 except myristic acid is used in place of acetic anhydride. The final purified peptide was further analyzed by mass spectroscopy (calculated mass=~1238, observed mass=1239.6).

EXAMPLE 5

Synthesis of Palmitoyl-Leu-Met-Tyr-Pro-Thr-Tyr-Leu-Lys-OH (DT-P1) (SEQ ID NO: 6)

The above peptide sequence was synthesized on resin in a similar way as described in Example 1 except palmitic acid is used in place of acetic anhydride. The final purified peptide was further analyzed by mass spectroscopy (calculated mass=~1262, observed mass=1263.4).

EXAMPLE 6

The cytotoxic effect of Lipo peptide analogs, DT-A1 (SEQ ID NO: 2), DT-B1 (SEQ ID NO: 3), DT-01 (SEQ ID NO: 4), DT-M1 (SEQ ID NO: 5) and DT-P1 (SEQ ID NO: 6) was studied by MTT assay which is based on the principle of uptake of MTT [3-[4,5-dimethylthiazol-2-yl]-2,5-diphenyl tetrazolium bromide], a tetrazolium salt by the metabolically active cells where it is metabolized by active mitochondria into a blue colored formazan product which can be read spectrophotometrically. Briefly, tumor cells PTC (primary colon) KB (Oral squamous), U87MG (Glioblastoma), HBL100 (Breast), HeP2 (Laryngeal), ECV304 (Endothelial), PA-1 (Ovary) and L132 (Lung) were incubated with the peptide analogs for 48 hours at 37° C. in a 96-well culture plate, followed by the addition of 100 µg MTT and _further incubation of 1 hour. The formazan crystals formed inside the cells were dissolved with a detergent comprising 10% Sodium dodecyl sulfate and 0.01 N HCl and optical density read on a multiscan ELISA reader. The optical density was directly proportional to the number of proliferating and metabolically active cells. Percent cytotoxicity of peptide analogs is shown in the following Tables.

| | DT-A1 | | | |
|---|---|---|---|---|
| | Percentage cytotoxicity at different concentrations | | | |
| Cell Line | 1 µM | 100 nM | 10 nM | 1 nM |
| KB | 21.0 ± 2.3 | 26.9 ± 2.1 | 31.0 ± 2.1 | 25.9 ± 1.6 |
| U87MG | 21.9 ± 1.4 | 26.9 ± 1.5 | 29.9 ± 2.2 | 10.4 ± 1.3 |
| HBL100 | 28.9 ± 1.2 | 30.5 ± 1.3 | 31.9 ± 3.5 | 19.9 ± 3.5 |
| HeP2 | 19.7 ± 1.1 | 21.9 ± 2.7 | 39.9 ± 1.8 | 14.9 ± 2.2 |
| L132 | 12.9 ± 2.4 | 14.6 ± 3.1 | 26.4 ± 3.2 | 13.9 ± 2.9 |
| PA-1 | 6.9 ± 3.2 | 18.5 ± 2.3 | 24.9 ± 2.6 | 21.9 ± 1.5 |
| ECV304 | 10.8 ± 3.4 | 22.0 ± 2.3 | 16.5 ± 3.4 | 8.0 ± 2.5 |

| | DT-B1 | | | |
|---|---|---|---|---|
| | Percentage cytotoxicity at different concentrations | | | |
| Cell Line | 1 µM | 100 nM | 10 nM | 1 nM |
| PTC | 31 ± 1.5 | 48 ± 1.7 | 44 ± 1.3 | 36 ± 1.0 |
| KB | 14.8 ± 2.3 | 18.9 ± 3.2 | 25.9 ± 4.1 | 21.9 ± 0.5 |
| U87MG | 20.6 ± 1.7 | 30.7 ± 1.7 | 39.7 ± 2.7 | 33.9 ± 0.6 |
| HBL100 | 32.8 ± 2.2 | 33.9 ± 2.8 | 34.8 ± 1.8 | 33.0 ± 1.5 |
| HeP2 | 12.9 ± 4.4 | 14.9 ± 5.3 | 22.9 ± 1.6 | 8.7 ± 1.5 |
| L132 | 11.8 ± 2.3 | 10.7 ± 2.6 | 26.8 ± 1.9 | 13.9 ± 1.9 |
| PA-1 | 33.7 ± 1.6 | 38.5 ± 1.6 | 45.8 ± 1.2 | 43.9 ± 2.9 |
| ECV304 | 25.8 ± 2.3 | 31.9 ± 2.8 | 19.9 ± 4.2 | 18.7 ± 5.3 |

DT-O1

Percentage cytotoxicity at different concentrations

| Cell Line | 1 μM | 100 nM | 10 nM | 1 nM |
|---|---|---|---|---|
| PTC | 29 ± 5.5 | 33 ± 3.2 | 32 ± 0.3 | 28 ± 5.4 |
| KB | 23.9 ± 1.3 | 26.9 ± 2.2 | 34.9 ± 3.1 | 21.0 ± 0.6 |
| U87MG | 21.9 ± 1.5 | 28.6 ± 1.2 | 38.7 ± 1.7 | 37.0 ± 1.6 |
| HBL100 | 27.4 c ± 2.7 | 32.8 ± 2.8 | 33.7 ± 2.8 | 30.0 ± 1.4 |
| HeP2 | 18.8 ± 4.2 | 17.9 ± 2.3 | 22.9 ± 1.2 | 8.6 ± 2.5 |
| L132 | 7.9 ± 2.3 | 14.9 ± 2.5 | 25.9 ± 1.7 | 19.4 ± 2.9 |
| PA-1 | 6.0 ± 1.4 | 22.6 ± 3.6 | 37.8 ± 2.2 | 26.0 ± 3.9 |
| ECV304 | 23.9 ± 2.2 | 24.9 ± 2.4 | 27.9 ± 3.2 | 16.9 ± 1.3 |

DT-M1

Percentage cytotoxicity at different concentrations

| Cell Line | 1 μM | 100 nM | 10 nM | 1 nM |
|---|---|---|---|---|
| PTC | 30 ± 3.9 | 31 ± 4.6 | 25 ± 3.6 | 26 ± 0.5 |
| KB | 12.9 ± 1.6 | 19.0 ± 3.2 | 23.9 ± 3.1 | 21.0 ± 26 |
| U87MG | 5.0 ± 2.5 | 32.2 ± 2.2 | 44.9 ± 2.7 | 29.4 ± 1.2 |
| HBL100 | 29.6 ± 2.3 | 30.4 ± 2.4 | 31.6 ± 3.8 | 21.9 ± 2.4 |
| HeP2 | 12.9 ± 1.2 | 22.9 ± 1.3 | 18.7 ± 2.2 | 15.8 ± 2.2 |
| L132 | 9.6 ± 2.4 | 16.8 ± 2.1 | 26.7 ± 1.1 | 10.6 ± 1.9 |
| PA-1 | 15.7 ± 1.2 | 25.9 ± 3.3 | 42.0 ± 2.2 | 27.5 ± 2.9 |
| ECV304 | 17.7 ± 1.2 | 22.9 ± 1.0 | 16.9 ± 3.1 | 21.9 ± 1.6 |

DT-P1

Percentage cytotoxicity at different concentrations

| Cell Line | 1 μM | 100 nM | 10 nM | 1 nM |
|---|---|---|---|---|
| PTC | 31 ± 3.1 | 33 ± 1.1 | 21 ± 1.2 | 27 ± 3.1 |
| KB | 18.0 ± 2.6 | 23.0 ± 2.2 | 32.0 ± 2.1 | 21.9 ± 2.6 |
| U87MG | 18.4 ± 2.4 | 32.9 ± 2.5 | 34.0 ± 2.6 | 9.6 ± 1.8 |
| HB100 | 28.9 ± 1.3 | 33.3 ± 1.4 | 34.9 ± 3.6 | 25.7 ± 2.5 |
| HeP2 | 14.9 ± 1.3 | 28.9 ± 1.7 | 24.9 ± 2.8 | 13.9 ± 1.2 |
| L132 | 17.8 ± 2.2 | 19.6 ± 1.1 | 29.0 ± 1.2 | 10.9 ± 1.9 |
| PA-1 | 21.7 ± 2.2 | 25.6 ± 3.3 | 21.9 ± 2.2 | 20.5 ± 1.9 |
| ECV304 | 25.9 ± 1.4 | 31.9 ± 1.3 | 19.9 ± 3.4 | 18.8 ± 2.6 |

EXAMPLE 7

In Vivo Activity of Lipo-Peptide Analogs

The antitumor activity of DT-B1 (SEQ ID NO: 3) was studied in human colon adenocarcinoma (PTC) xenografts in nude mice. PTC tumor xenografts were grown in Balb/c a thymic mice by subcutaneous inoculation of a single cell suspension of PTC cells ($15 \times 10^6$ cells/100 EL). The tumor bearing animals were divided into 2 groups of three animals each including one group comprising untreated control animals. Treatment with DT-B1 was initiated when the average tumor volumes, as measured using a vernier caliper, were between 1.3 $cm^3$. Solutions of DT-B1 was prepared at a concentration of 126 μg/ml and intravenously administered to the assigned group of tumor bearing animals at a dose of 12.6 μg/100 μL twice a day so that the total dose of 25.2 μg/day was administered to each animal. The treatment was continued for a period of 14 days.

The antitumor activity of the compounds was monitored by measuring tumor volumes every fourth day using the formula W*W*L*0.4 (W=smaller diameter, L=larger diameter). The percentage inhibition of tumor growth was calculated using the formula (1-tumor volume-treated/tumor volume-control)* 100. FIG. 1 shows the tumor kinetics till day 20 in the treated and untreated animals. DT-B1 showed a significant antitumor activity on PTC xenografts. The percentage inhibition of tumor growth caused by DT-B1 as compared to controls on day 20 was 95.85%.

All publications referenced are incorporated by reference herein, 6: including the amino acid sequences listed in each publication. All the compounds disclosed and referred to in the publications mentioned above are incorporated by reference herein, including those compounds disclosed and referred to in articles cited by the 10 publications mentioned.

What is claimed is:

1. A peptide of the sequence X-Leu-Met-Tyr-Pro-Thr-Tyr-Leu-Lys-Y wherein X is selected from the group consisting of acetyl, n-butanoyl, n-hexanoyl, n-octanoyl, lauroyl, myristoyl, palmitoyl, isohexanoyl, cyclohexanoyl, cyclopentylcarbonyl, n-heptanoyl, n-decanoyl, n-undecanoyl and 3,7-dimethyloctanoyl and Y is a carboxy terminal residue selected from OH or amino; or a pharmaceutically acceptable salt thereof.

2. A pharmaceutical composition comprising the peptide of claim 1 and a pharmaceutically acceptable carrier.

3. A method for treating a cancer selected from the group consisting of colon, oral, glioblastoma, breast, laryngeal, endothelial, ovarian and lung comprising administering to a patient in need thereof a peptide according to claim 2 in an amount effective to treat the cancer.

4. A peptide of the sequence Acetyl-Leu-Met-Tyr-Pro-Thr-Tyr-Leu-Lys-OH (SEQ ID NO:2) or a pharmaceutically acceptable salt thereof.

5. A pharmaceutical composition comprising the peptide of claim 4 and a pharmaceutically acceptable carrier.

6. A method for treating a cancer selected from the group consisting of colon, oral, glioblastoma, breast, laryngeal, endothelial, ovarian and lung comprising administering to a patient in need thereof a peptide according to claim 5 in an amount effective to treat the cancer.

7. A peptide of the sequence n-Butanoyl-Leu-Met-Tyr-Pro-Thr-Tyr-Leu-Lys-OH (SEQ ID NO:3) or a pharmaceutically acceptable salt thereof.

8. A pharmaceutical composition comprising the peptide of claim 7 and a pharmaceutically acceptable carrier.

9. A method for treating a cancer selected from the group consisting of colon, oral, glioblastoma, breast, laryngeal, endothelial, ovarian and lung comprising administering to a patient in need thereof a peptide according to claim 8 in an amount effective to treat the cancer.

10. A peptide of the sequence n-Octanoyl-Leu-Met-Tyr-Pro-Thr-Tyr-Leu-Lys-OH (SEQ ID NO:4) or a pharmaceutically acceptable salt thereof.

11. A pharmaceutical composition comprising the peptide of claim 10 and a pharmaceutically acceptable carrier.

12. A method for treating a cancer selected from the group consisting of colon, oral, glioblastoma, breast, laryngeal, endothelial, ovarian and lung comprising administering to a patient in need thereof a peptide according to claim 11 in an amount effective to treat the cancer.

13. A peptide of the sequence Myristoyl-Leu-Met-Tyr-Pro-Thr-Tyr-Leu-Lys-OH (SEQ ID NO:5) or a pharmaceutically acceptable salt thereof.

14. A pharmaceutical composition comprising the peptide of claim 13 and a pharmaceutically acceptable carrier.

15. A method for treating a cancer selected from the group consisting of colon, oral, glioblastoma, breast, laryngeal, endothelial, ovarian and lung comprising administering to a patient in need thereof a peptide according to claim 14 in an amount effective to treat the cancer.

16. A peptide of the sequence Palmitoyl-Leu-Met-Tyr-Pro-Thr-Tyr-Leu-Lys-OH (SEQ ID NO:6) or a pharmaceutically acceptable salt thereof.

17. A pharmaceutical composition comprising the peptide of claim 16 and a pharmaceutically acceptable carrier.

18. A method for treating a cancer selected from the group consisting of colon, oral, glioblastoma, breast, laryngeal, endothelial, ovarian and lung comprising administering to a patient in need thereof a peptide according to claim 17 in an amount effective to treat the cancer.

19. The method according to any one of claims 3 to 18 further comprising administering a second different peptide of the sequence X-Leu-Met-Tyr-Pro-Thr-Tyr-Leu-Lys-Y wherein X is selected from the group consisting of acetyl, n-butanoyl, n-hexanoyl, n-octanoyl, lauroyl, myristoyl, palmitoyl, isohexanoyl, cyclohexanoyl, cyclopentylcarbonyl, n-hepatonoyl, n-undecanoyl and 3,7-dimethyloctanoyl and Y is a carboxy terminal residue selected from OH or amino; or a pharmaceutically acceptable salt thereof or an anticancer compound.

* * * * *

SEQUENCE LISTING

<160> NUMBER OF SEQ ID NOS: 6

<210> SEQ ID NO 1
<211> LENGTH: 8
<212> TYPE: PRT
<213> ORGANISM: Sus barbatus

<400> SEQUENCE: 1

Leu Met Tyr Pro Thr Tyr Leu Lys
1               5

<210> SEQ ID NO 2
<211> LENGTH: 8
<212> TYPE: PRT
<213> ORGANISM: Artificial Sequence
<220> FEATURE:

```
<223> OTHER INFORMATION: Description of Artificial Sequence: This
      peptide was synthetically generated
<221> NAME/KEY: MOD_RES
<222> LOCATION: (1)
<223> OTHER INFORMATION: /product = Acetyl-leucine/label = Acetyl-Leu

<400> SEQUENCE: 2

Xaa Met Tyr Pro Thr Tyr Leu Lys
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (1)
<223> OTHER INFORMATION: /product = n-Butanoyl-leucine/label =
      n-Butanoyl-Leu

<400> SEQUENCE: 3

Xaa Met Tyr Pro Thr Tyr Leu Lys
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: This
      peptidewas synthetically generated
<221> NAME/KEY: MOD_RES
<222> LOCATION: (1)
<223> OTHER INFORMATION: /product = n-Octanoyl-leucine/label =
      n-Octanoyl-Leu

<400> SEQUENCE: 4

Xaa Met Tyr Pro Thr Tyr Leu Lys
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (1)
<223> OTHER INFORMATION: /product = Myristoyl-leucine/label =
      Myristoyl-Leu

<400> SEQUENCE: 5

Xaa Met Tyr Pro Thr Tyr Leu Lys
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated
```

-continued

```
<221> NAME/KEY: MOD_RES
<222> LOCATION: (1)
<223> OTHER INFORMATION: /product = Palmitoyl-leucine/label =
      Palmitoyl-Leu

<400> SEQUENCE: 6

Xaa Met Tyr Pro Thr Tyr Leu Lys
1               5
```